United States Patent [19]

Ogawa et al.

[11] Patent Number: 5,334,225
[45] Date of Patent: Aug. 2, 1994

[54] KERATINOUS FIBER DYE COMPOSITION CONTAINING A 2-SUBSTITUTED AMINO-5-ALKYLPHENOL DERIVATIVE COUPLER

[75] Inventors: Masahiko Ogawa; Hidetoshi Tagami; Toru Yoshihara; Jiro Kawase, all of Tokyo; Akira Kiyomine, Tochigi; Tadashi Tamura, Tochigi; Yoshinori Nishizawa, Tochigi; Ken-ichi Matsunaga, Saitama, all of Japan

[73] Assignee: Kao Corporation, Tokyo, Japan

[21] Appl. No.: 90,963

[22] Filed: Jul. 13, 1993

[30] Foreign Application Priority Data

Jul. 15, 1992 [JP] Japan .................... 4-187691

[51] Int. Cl.⁵ .................... A61K 7/13; C07C 271/00
[52] U.S. Cl. .................... 8/408; 8/405; 8/406; 8/407; 8/410; 8/412; 8/421; 564/218; 564/52; 560/250; 560/29
[58] Field of Search .......... 8/405, 406, 407, 408, 8/410, 412, 421; 564/443, 218, 52; 560/250, 29

[56] References Cited

U.S. PATENT DOCUMENTS

| | | |
|---|---|---|
| 3,712,790 | 1/1973 | Kalopissis et al. .................. 564/443 |
| 3,948,596 | 4/1976 | Kalopissis et al. .................. 8/412 |
| 4,035,422 | 7/1977 | Kalopissis et al. .................. 564/443 |
| 4,310,693 | 1/1982 | Fujita et al. .................. 564/443 |
| 5,214,194 | 5/1993 | Tang et al. .................. 564/443 |

*Primary Examiner*—Paul Lieberman
*Assistant Examiner*—Caroline L. Dusheck
*Attorney, Agent, or Firm*—Sughrue, Mion, Zinn, Macpeak & Seas

[57] ABSTRACT

A keratinous fiber dye composition comprising a developer and a coupler, wherein the coupler is a 2-substituted amino-5-alkylphenol derivative represented by the following formula (1):

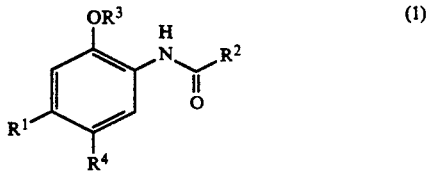

wherein the all symbols are defined in the disclosure, is disclosed. The keratinous fiber dye composition imparts a color tone of a high chroma and is excellent in coloring power and fastness.

4 Claims, No Drawings

KERATINOUS FIBER DYE COMPOSITION CONTAINING A 2-SUBSTITUTED AMINO-5-ALKYLPHENOL DERIVATIVE COUPLER

FIELD OF THE INVENTION

This invention relates to a keratinous fiber dye composition which is excellent in chroma, coloring power and fastness.

BACKGROUND OF THE INVENTION

In order to dye keratinous fibers such as the hair, there have been widely used so-called oxidation dyes comprising a combination of a developer with a coupler. Dyeing with such an oxidation dye is performed by utilizing the ability of a so-called oxidation colorant, which is formed by the oxidation coupling between a developer and a coupler, to strongly dye, for example, the hair.

Examples of these developer which have been generally used include p-phenylenediamine derivatives, p-aminophenol derivatives, diaminopyridine derivatives, 4-aminopyrazolone derivatives and heterocyclic hydrazone derivatives. Examples of the couplers which have been employed include α-naphthol, o-cresol, m-cresol, 2,6-dimethylphenol, 2,5-dimethylphenol, 3,4-dimethylphenol, 3,5-dimethylphenol, benzcatechin, pyrogallol, 1,5-dihydroxynaphthalene, 1,7-dihydroxynaphthalene, 5-amino-2-methylphenol, hydroquinone, 2,4-diaminoanisole, m-toluylenediamine, o-aminophenol, resorcin, resorcin monomethyl ether, m-phenylenediamine, 1-phenyl-3-methyl-5-pyrazolone, 1-phenyl-3-amino-5-pyrazolone, 1-phenyl-3,5-diketopyrazolidine, 1-methyl-7-dimethylamino-4-hydroxyquinolon-2-one, 1-amino-3-acetylacetoamino-4-nitrobenzole, m-aminophenol, 4-chlororesorcin, 2-methylresorcin, 2,4-diaminophenoxyethanol, 2,6-diaminopyridine, 3,5-diaminotrifluoromethylbenzene, 2,4-diaminofluorobenzene, 3,5-diaminofluorobenzene, 2,4-diamino-6-hydroxypyrimidine, 2,4,6-triaminopyrimidine, 2-amino-4,6-dihydroxypyrimidine, 4-amino-2,6-dihydroxypyrimidine, 4,6-diamino-2-hydroxypyrimidine, p-nitro-o-phenylenediamine, 2-amino-5-nitrophenol, p-nitro-m-phenylenediamine, o-nitro-p-phenylenediamine and 2-amino-4-nitrophenol.

However conventional oxidation dyes are not always satisfactory in chroma, coloring power or fastness.

In the case of dyes for bluish colors, for example, m-phenylenediamine or 2,6-diaminopyridine can impart a color tone of a high chroma when used as a coupler. However, it is disadvantageous in serious color change/fading after dyeing or discoloration after shampooing. That is to say, there have been known hitherto only a few keratinous fiber dye compositions being satisfactory in all of chroma, coloring power and fastness.

SUMMARY OF THE INVENTION

Accordingly, it is an object of the present invention to provide a keratinous fiber dye composition which is excellent in all of chroma, coloring power and fastness.

Under the above-mentioned circumstances, the present inventors have paid their attention to the fact that the chroma, coloring power and fastness largely depend on the characteristics of a coupler. Thus they have synthesized a number of compounds and examined the properties thereof as a coupler. As a result, they have successfully found that when a 2-substituted amino-5-alkylphenol derivative represented by the following formula (1) is used as a coupler, a keratinous fiber dye composition capable of imparting a color tone of a high chroma and being excellent in coloring power and fastness can be obtained, thus completing the present invention.

Accordingly, the present invention provides a keratinous fiber dye composition comprising a developer and a coupler wherein said coupler is a 2-substituted amino-5-alkylphenol derivative represented by the following formula (1):

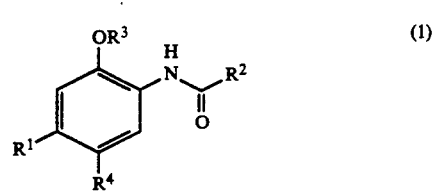

wherein $R^1$ represents an alkyl group having from 1 to 4 carbon atoms; $R^2$ represents a hydrogen atom, a substituted or unsubstituted alkyl group having from 1 to 4 carbon atoms, a substituted or unsubstituted alkoxy group having from 1 to 4 carbon atoms or a substituted or unsubstituted amino group; $R^3$ represents a hydrogen atom or a substituted or unsubstituted acyl group having from 2 to 5 carbon atoms; and $R^4$ represents a hydrogen atom, a halogen atom, or an alkoxy group having from 1 to 4 carbon atoms which may be substituted with a hydroxyl group; or a cosmetically acceptable salt thereof.

DETAILED DESCRIPTION OF THE INVENTION

Examples of the alkyl groups having from 1 to 4 carbon atoms represented by $R^1$ and $R^2$ in the 2-substituted amino-5-alkylphenol derivative of formula (1) which is to be used as a coupler in the present invention include methyl, ethyl, n-propyl, isopropyl, n-butyl, sec-butyl and tert-butyl groups.

Examples of the alkoxy group having from 1 to 4 carbon atoms represented by $R^2$ and $R^4$ include methoxy, ethoxy, n-propoxy, isopropoxy, n-butoxy, sec-butoxy and tert-butoxy groups.

Examples of the acyl group having from 2 to 5 carbon atoms represented by $R^3$ include acetyl, propanoyl, 2,2-dimethylpropanoyl, 3-methylpropanoyl, butanoyl, 2-methylbutanoyl and pentanoyl groups.

Examples of the halogen atom represented by $R^4$ include fluorine, chlorine, bromine and iodine atoms.

Among these groups, methyl or ethyl group is preferred as the group represented by $R^1$, methyl, ethyl, methoxy or amino group is preferred as the group represented by $R^2$, hydrogen atom, acetyl or propanoyl group is preferred as the group represented by $R^3$, and hydrogen atom or methoxy group is preferred as the group represented by $R^4$.

Examples of the substituent which may substitute on the alkyl and alkoxy groups represented by $R^2$ and the acyl group represented by $R^3$ include halogen atoms (e.g., fluorine atom, chlorine atom, bromine atom, iodine atom), alkoxy groups having from 1 to 4 carbon atoms (e.g., methoxy, ethoxy, n-propoxy, isopropoxy, n-butoxy, sec-butoxy, tert-butoxy), alkanoyloxy groups having from 2 to 5 carbon atoms (e.g., acetoxy, propanoyloxy, 2,2-dimethylpropanoyloxy, 3-methylpropanoyloxy, butanoyloxy, 2-methylbutanoyloxy, pentanoyloxy), hydroxyl group, amino group which may be substituted by a protecting group, carboxyl group and alkoxy-carbonyl groups having from 2 to 5 carbon atoms (e.g., methoxycarbonyl, ethoxycarbonyl, n-propoxycarbonyl, isopropoxycarbonyl, n-butoxycarbonyl, sec-butoxycarbonyl, tert-butoxycarbonyl). Examples of the protecting group which may substitute on the amino group include tert-butoxycarbonyl and benzyloxycarbonyl groups. Among these substituents, methoxy and hydroxy groups are preferred.

Examples of the substituent which may substitute on the amino group represented by $R^2$ include alkyl groups having from 1 to 4 carbon atoms (e.g., methyl, ethyl, n-propyl, isopropyl, n-butyl, sec-butyl, tert-butyl) optionally substituted with hydroxyl groups. Among these, hydroxyethyl groups is preferred.

The alkyl and alkoxy groups represented by $R^2$ and the acyl group represented by $R^3$ may be substituted with one or more of these substituents.

The compound (1) can be prepared by, for example, the following method.

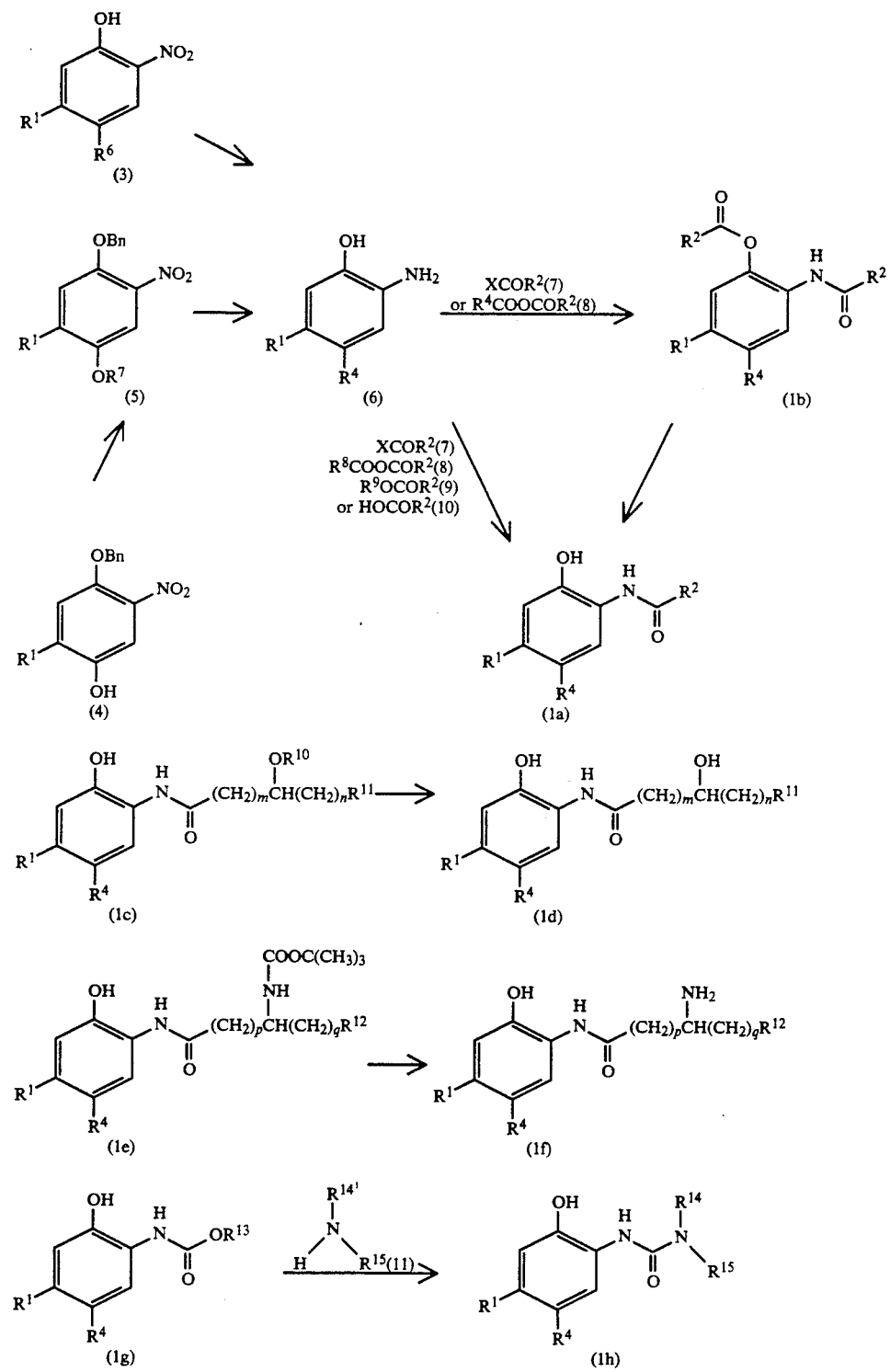

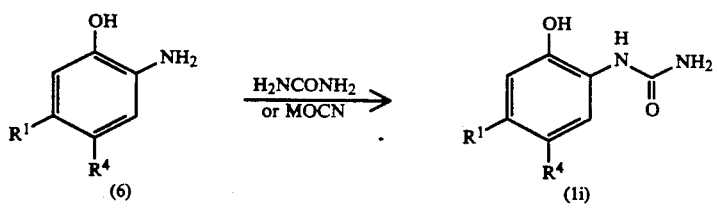

In the above formulae, $R^1$, $R^2$ and $R^4$ are as defined above. $R^6$ represents a hydrogen or halogen atom. $R^7$ represents an alkyl group having from 1 to 4 carbon atoms which may be substituted with hydroxyl groups. $R^8$, $R^9$, $R^{10}$ and $R^{13}$ represent each a substituted or unsubstituted alkyl group having from 1 to 4 carbon atoms. $R^{11}$ and $R^{12}$ represents each a hydrogen atom or a methyl group. $R^{14}$ and $R^{15}$ may be either the same or different from each other and represent each a hydrogen atom or an alkyl group having from 1 to 4 carbon atoms which may be substituted with hydroxyl groups. X represents a chlorine, bromine or iodine atom. M represents metal sodium or metal potassium. m, n, p and q each independently represents an integer of from 0 to 3, provided that neither m+n nor p+q exceeds 4.

That is to say, a 5-alkyl-2-nitrophenol derivative (3), which is obtainable by a method described in, for example, JP-A-50-149633 (the term "JP-A" as used herein means a "unexamined published Japanese Patent Application"), is reduced or a 2-alkyl-4-benzyloxy-5-nitrophenol derivative (4), which is obtainable by a method described in, for example, JP-A-62-240960, is reacted with a dialkyl sulfate, an alkyl halide or an alkylene oxide to give the compound (5), followed by reduction to give thereby the compound (6). The compound (6) is then reacted with the compound (7), (8), (9) or (10) to give thereby the compound (1a). Alternately, the compound (6) is reacted with at least two equivalents of the compound (7) or (8) to give thereby the compound (1b). The compound (1b) may be reacted with a base to give thereby the compound (1a). The compound (1c) obtained by the above method may be treated with a base to give thereby the compound (1d). By treating the compound (1e) with an acid, the compound (1f) is obtained. Further, by reacting the compound (1g) with an amine (11), the compound (1h) is obtained. When the compound (6) is reacted with urea or an alkali metal cyanate, the compound (1i) is obtained.

The compound (3) can be reduced by a method commonly employed for reducing nitro group. A reducing method with the use of acetic acid-iron or hydrochloric acid-tin and a catalytic hydrogenation method are convenient and efficient therefor. The compound (4) can be alkylated in the presence of a base such as sodium hydroxide, potassium hydroxide, sodium carbonate or potassium carbonate. The compound (5) can be conveniently and efficiently reduced by catalytic hydrogenation. As a catalyst to be used for the catalytic hydrogenation of the compounds (3) and (5), palladium, platinum, copper and nickel are usable. It is recommended to use methanol, ethanol, ethyl acetate or N,N-dimethylformamide as a solvent therefor. After the completion of the reduction, the catalyst is filtered off and the filtrate is concentrated and subjected to, for example, recrystallization or sublimation. Thus the compound (6) can easily be purified. Alternately, the unpurified filtrate can be directly used in the subsequent reaction after separating the catalyst.

To obtain the compound (1a) directly from the compound (6) and the compound (7) or (8), the compound (6) may be reacted with the compound (7) or (8) in the presence or absence of a base in accordance with a known acylating reaction. Examples of the base include calcium carbonate and sodium carbonate. As a solvent, it is preferable to use water, methanol, ethanol, dioxane, a mixture thereof, methylene chloride or chloroform.

The reaction between the compound (6) and the compound (9) may be preferably carried out in the presence of a base such as a metal alkoxide without using any solvent or by using a solvent such as tetrahydrofuran, toluene or xylene. The reaction can be efficiently carried out by distilling off the alcohol formed by the reaction. However, this reaction may be carried out in an alcoholic solvent such as methanol or ethanol.

The reaction between the compound (6) and the compound (10) can be carried out by using a known condensing reagent such as N,N'-dicyclohexylcarbodiimide in a solvent such as methylene chloride, tetrahydrofuran, ethyl acetate, N,N-dimethylformamide or a mixture thereof. In order efficiently perform the reaction, a known additive such as 1-hydroxybenzotriazole may be used.

To obtain the compound (1b) from the compound (6), sulfuric acid may be used as a catalyst together with at least two equivalents of the compound (8) as a solvent. Alternately, the compound (6) may be reacted with at least two equivalents of the compound (7) or (8) in the presence of a base such as pyridine or triethylamine. The compound (1b) can easily be converted into the compound (1a) by reacting with an alkali such as sodium hydroxide or potassium hydroxide in a solvent such as water, methanol, ethanol or a mixture thereof.

To obtain the compound (1d) from the compound (1c), the same method as the one employed for obtaining the compound (1a) from the compound (1b) can be used. To obtain the compound (1f) from the compound (1e), an acid such as hydrochloric acid, hydrobromic acid, methanesulfonic acid, trifluoroacetic acid or trifluoromethanesulfonic acid may be used.

The reaction between the compound (1 g) and the amine (11) can be performed in the presence of a base such as a metal alkoxide.

The reaction between the compound (6) and urea or an alkali metal cyanate may be performed in accordance with a conventional method for synthesizing a substituted urea (for example, by heating in the presence of hydrochloric acid or acetic acid).

The compound (1) can easily be purified by, for example, recrystallization or column chromatography.

In order to improve the handling characteristics in preparation procedures, the compound (1) thus obtained can be formulated into an inorganic or organic salt (for example, hydrochloride, sulfate, phosphate, acetate, propionate, lactate, citrate) by a conventional method.

In the present invention, developers which are commonly employed in oxidation dyes are usable. Examples thereof include compounds represented by the following formula (2):

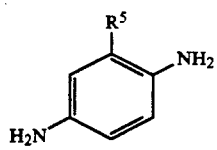

wherein $R^5$ represents a hydrogen atom, a methyl group, a methoxy group or a chlorine atom; and compounds such as N-phenyl-p-phenylenediamine, N,N-bis(2-hydroxyethyl)-p-phenylenediamine, p-aminophenol, p-methylaminophenol, o-aminophenol, 2,4-diaminophenol, 2,5-diaminopyridine, tetraaminopyridine and 4,4'-diaminodiphenylamine.

Among these compounds, p-phenylenediamine, toluene-2,5-diamine, o-methoxy-p-phenylenediamine and o-chloro-p-phenylenediamine, each represented by formula (2), are preferred.

Regarding the composition ratio of the developer to the coupler in the keratinous fiber dye composition according to the present invention, one component may be used in excess to another. The molar ratio of the developer to the coupler may preferably range from about 1:0.5 to about 1:2. Both of the developer and coupler can be used either singly or in combination of two or more of them.

The dye composition of the present invention may further contain known couplers and common direct dyes, if they are necessary in order to give the desired color tone.

Examples of such direct dyes include those described in *Senshoku Genryo Kijun* (Dye Material Standards) published by Japan Hair Color Industrial Association (for example, 2-amino-4-nitrophenol, 2-amino-5-nitrophenol, nitro-p-phenylenediamine hydrochloride, nitro-p-phenylenediamine, p-aminophenylsulfamic acid, p-nitro-o-phenylenediamine, picramic acid, sodium picramate, picric acid, Chrome Brown RH, hematein, nitro-p-phenylenediamine sulfate, p-nitro-o-phenylenediamine sulfate, p-nitro-m-phenylenediamine sulfate, 1-amino-4-methylaminoanthraquinone, 1,4-diaminoanthraquinone), acid dyes (for example, Red No. 2, Red No. 3, Red No. 102, Red No. 104, Red No. 105, Red No. 106, Yellow No. 4, Yellow No. 5, Green No. 3, Blue No. 1, Blue No. 2, Red No. 201, Red No. 227, Red No. 230, Red No. 231, Red No. 232, Orange No. 205, Orange No. 207, Yellow No. 202, Yellow No. 203, Green No. 201, Green No. 204, Green No. 205, Blue No. 202, Blue No. 203, Blue No. 205, Brown No. 201, Red No. 401, Red No. 502, Red No. 503, Red No. 504, Red No. 506, Orange No. 402, Yellow No. 402, Yellow No. 403, Yellow No. 406, Yellow No. 407, Green No. 401, Green No. 402, Purple No. 401, Black No. 401, as specified in *Hotei Sikiso Handbook* (Legal Dye Handbook), published by Nihon Keshohin Kogyo Rengokai), oil-soluble dyes (for example, Red No. 215, Red No. 218, Red No. 225, Orange No. 201, Orange No. 206, Yellow No. 201, Yellow No. 204, Green No. 202, Purple No. 201, Red No. 501, Red No. 505, Orange No. 403, Yellow No. 404, Yellow No. 405, Yellow No. 403, as specified in *Hotei Sikiso Handbook*), basic dyes (for example, Red No. 213, Red No. 214, as specified in *Hotei Sikiso Handbook*) and basic dyes manufactured by Arianor (for example, Sienna Brown, Mahogany, Madder Red, Steel Blue, Steaw Yellow). Among these dyes, nitrophenylenediamine, nitroaminophenol and anthraquinone dyes are preferred.

The oxidation coupling of the keratinous fiber dye composition according to the present invention is induced by atmospheric oxygen and thus, for example, the hair is dyed. However, it is preferable to add a chemical oxidation agent to thereby induce the oxidation coupling. Preferred examples of the oxidation agent include hydrogen peroxide, products obtained by an addition reaction of hydrogen peroxide to urea, melamine or sodium borate, and mixtures of these hydrogen peroxide adducts with potassium peroxide disulfate.

In general, the keratinous fiber dye composition of the present invention may preferably be provided in the form of, for example, a cream, an emulsion, a gel or a solution. These preparations can be obtained by adding wetting agents (emulsifiers), solubilizers, thickeners, stabilizers, texture-improvers, hair styling bases and perfumes, which are commonly employed in the field of cosmetics, to the abovementioned developer and coupler and treating the blend thus obtained by a conventional method. Examples of the wetting agents (emulsifiers) usable herein include alkyl benzenesulfonates, aliphatic alcohol sulfates, alkyl sulfonates, fatty acid alkanolamides and ethylene oxide/aliphatic alcohol adducts. Examples of the thickeners include methylcellulose, starch, higher aliphatic alcohols, paraffin oil and fatty acids. Examples of the stabilizers include reducing agents such as sulfites, hydroquinone derivatives and chelating agents. Examples of the texture-improvers and the hair styling bases include oils such as silicone, higher alcohols and various nonionic surfactants and various cationic polymers.

The total content of the developer and coupler in these preparations may range from 0.001 to 10% by weight, preferably from 0.01 to 5% by weight. It is generally preferable to use from 0.5 to 30% by weight of wetting agent(s) (emulsifiers) and from 0.1 to 25% by weight of thickener(s).

In these formulations, the pH value of the total composition is preferably adjusted to about 6 to about 11.

In order to dye keratinous fiber with the use of the keratinous fiber dye composition according to the present invention, an oxidation agent is first added to the keratinous fiber dye composition of the present invention to thereby perform oxidation coupling, thus preparing a dyeing solution. Next, this dyeing solution is applied to the keratinous fiber. After allowing to stand for 5 to 50 minutes, preferably about 25 to about 30 minutes as a function time, the keratinous fiber is washed and dried. The dyeing solution is applied at a temperature of from 15° to 40° C.

The keratinous fiber dye composition according to the present invention is capable of imparting a color tone of a high chroma to keratinous fibers and being excellent in coloring power and fastness.

To further illustrate the present invention in greater detail, and not by way of limitation, the following Example will be given. Unless otherwise indicated, all percents are by weight.

EXAMPLE 1

To an autoclave, there were fed 1.5 g of palladium carbon, 50.0 g (moisture content: 5.9%; 308 mmol) of 5-methyl-2-nitrophenol and 250 ml of methanol. The mixture was stirred under a hydrogen pressure of 20 kg/cm$^2$ at 50° C. for 3 hours. After cooling, the catalyst was filtered and washed with 50 ml of warm methanol twice and the washing liquor was combined with the filtrate. After distilling off the solvent under reduced pressure, the residue was dried. Thus 37.3 g (303 mmol) of 6-amino-m-cresol was obtained as a brown solid. The yield was 98%. A 15.0 g portion of this brown solid product was recrystallized from 45 ml of isopropanol. Thus 11.9 of 6-amino-m-cresol was obtained as yellow crystals. The recovering yield was 79%.

EXAMPLE 2

To 20 ml of ethanol, there were added under ice-cooling 4.83 g of sodium methoxide and 18.0 g of ethyl formate. Further, 10.0 g (81.3 mmol) of 6-amino-m-cresol was added thereto under ice-cooling. After putting back to room temperature, the solution was stirred under a nitrogen atmosphere for 1 hour. After the completion of the reaction, the reaction mixture was poured into 200 ml of water. The obtained solution was neutralized with glacial acetic acid, extracted with 300 ml of ethyl acetate, washed with 200 ml of 1N hydrochloric acid and 100 ml of a saturated aqueous solution of sodium hydrogencarbonate and dried over anhydrous Glauber's salt. After distilling off the solvent under reduced pressure, 3.98 g (26.4 mmol) of N-(2-hydroxy-4-methylphenyl)formamide was obtained as a pale brown solid. The yield was 32%.

$^1$H-NMR spectrum (200 MHz, DMSO-d$_6$): δppm:
cis-isomer: 2.18 (3H, s), 6.56 (1H, d, J=8.1 Hz), 6.68 (1H, s), 7.87 (1H, d, J=8.1 Hz), 8.24 (1H, d, J=1.8 Hz), 9.51 (1H, brs), 10.19 (1H, s)
trans-isomer: 2.18 (3H, s), 6.56 (1H, d, J=7.9 Hz), 6.68 (1H, s), 6.98 (1H, d, J=7.9 Hz), 8.41 (1H, d, J=11.3 Hz), 9.21 (1H, d, J =11.3 Hz), 10.19 (1H, s)

In a dimethylformamide solution, this compound exists as a 10:1 mixture of the cis-isomer and the trans-isomer regarding the amide bond.

EXAMPLE 3

To 100 ml of dioxane, there were added 11.78 g (95.8 mmol) of 6-amino-m-cresol and 4.99 g (49.9 mmol) of calcium carbonate. Further, 9.51 g (100.6 mmol) of methyl chloroformate was added thereto over 10 minutes under cooling in an ice bath. After putting back to room temperature, the mixture was stirred for additional 1 hour. After the completion of the reaction, 100 ml of acetone was added. The inorganic salt was filtered off and the solvent was distilled off from the filtrate under reduced pressure. Thus 11.52 g (68.2 mmol) of N-(2-hydroxy-4-methylphenyl)methylcarbamate was obtained as a brown solid. The yield was 71%. After recrystallizing from acetonitrile, 3.83 g of N-(2-hydroxy-4-methylphenyl)methylcarbamate was obtained as pale purple crystals. The recovering yield was 33%.

$^1$H-NMR spectrum (200 MHz, DMSO-d$_6$): δppm:
217 (3H, s), 3.06 (3H, s), 6.55 (1H, d, J=8.0 Hz), 6.63 (1H, s), 7.33 (1H, d, J=8.0 Hz), 8.21 (1H, s), 9.50 (1H, s)

EXAMPLE 4

To 13 ml of water, there were added 5.00 g (40.7 mmol) of 6-amino-m-cresol, 9.76 g of (162.6 mmol) of urea, 4 ml of conc. hydrochloric acid and 0.8 ml of a mixture (1:1 (v:v)) of conc. hydrochloric acid and glacial acetic acid, followed by heating under reflux for 1.5 hours. After cooling, 20 ml of water was added. The crystals thus precipitated were filtered and dried to thereby give 5.81 g (35.0 mmol) of N-(2-hydroxy-4-methylphenyl)urea as dark brown crystals. The yield was 86%. After recrystallizing from acetonitrile, 2.00 g of N-(2-hydroxy-4-methylphenyl)urea was obtained as pale purple crystals. The recovering yield was 34%.

$^1$H-NMR spectrum (200 MHz, DMSO-d$_6$): δppm:
2.14 (3H, s), 6.13 (2H, s), 6.49 (1H, d, J=8.1 Hz), 6.59 (1H, s), 7.61 (1H, d, J=8.1 Hz), 7.90 (1H, s), 9.82 (1H, s)

EXAMPLE 5

To 15 ml of toluene, there were added 4.0 g (32.5 mmol) of N-(2-hydroxy-4-methylphenyl)methylcarbamate, 4.58 g (7.50 mmol) of 2-aminoethanol and 1.93 g (35.8 mmol) of sodium methoxide, followed by stirring at 100° C. for 30 minutes. After cooling, the reaction mixture was poured into 150 ml of water. The toluene layer was removed and the aqueous layer was neutralized with glacial acetic acid. The crystals thus precipitated were filtered off. The filtrate was extracted with 200 ml of ethyl acetate, concentrated under reduced pressure and subjected to silica gel column chromatography (Si60 manufactured by Merck; 230–400 mesh; 200 g; eluent: 5% methanol-chloroform (2,000 ml), 10% methanol-chloroform (2,000 ml)). The fraction of 0 to 1,200 ml of 10% methanol-chloroform was distilled under reduced pressure and dried. Thus 0.20 g (1.0 mmol) of N-(2-hydroxy-4-methylphenyl)-N'-(2-hydroxyethyl)urea was obtained as a pale brown solid. The yield was 3%.

$^1$H-NMR spectrum (200 MHz, DMSO-d$_6$): δppm:
2.14 (3H, s), 3.12 (2H, td, J=5.6, 5.5 Hz), 3.41 (2H, td, J=5.6, 5.1 Hz), 4.72 (1H, t, J=5.1 Hz), 6.49 (1H, d, J=8.2 Hz), 6.59 (1H, s), 6.83 (1H, t, J=5.5 Hz), 7.62 (1H, d, J=8.2 Hz), 7.91 (1H, s), 9.74 (1H, s)

EXAMPLE 6

To a mixture of 40 ml of ethanol with 60 ml of water, there was added 20.0 g (16.3 mmol) of 6-amino-m-cresol, followed by heating to 80° C. To the obtained solution, there was added dropwise 17.4 g (17.1 mmol) of acetic anhydride over 10 minutes and the mixture was stirred at 80° C. for 15 minutes. After the completion of the reaction, the mixture was cooled to 10° C. The crystals thus precipitated were filtered, washed with water and dried. Thus 23.9 g (15.0 mmol) of N-(2-hydroxy-4-methylphenyl)acetamide was obtained as pale brown crystals. The yield was 89%. A 20.0 g portion of this product was recrystallized from acetonitrile to thereby give 17.9 g of N-(2-hydroxy-4-methylphenyl)acetamide as colorless crystals. The recovering yield was 90%.

$^1$H-NMR spectrum (200 MHz, DMSO-d$_6$): δppm:
2.07 (3H, s), 2.19 (3H, s), 6.56 (1H, d, J=8.0 Hz), 6.66 (1H, s), 7.45 (1H, d, J=8.0 Hz), 9.28 (1H, s), 9.60 (1H, s)

EXAMPLE 7

To 130 ml of dioxane, were added 20.0 g (163 mmol) of 6-amino-m-cresol and 9.2 g (92 mmol) of calcium carbonate, followed by heating to 60° C. To the obtained solution, there was added 22.1 g (196 mmol) of chloroacetyl chloride over 40 minutes and the mixture was further stirred at 60° C. for 2 hours. After cooling, the mixture was poured into 500 ml of water, extracted with 700 ml of ethyl acetate and dried over anhydrous Glauber's salt. After distilling off the solvent under reduced pressure, the obtained greenish brown solid was recrystallized from acetonitrile. Thus 23.5 g (118 mmol) of N-(2-hydroxy-4-methylphenyl)chloroacetamide was obtained as pale green crystals. The yield was 72%.

$^1$H-NMR spectrum (200 MHz, DMSO-d$_6$): δppm: 2.20 (3H, s), 4.36 (2H, s), 6.59 (1H, d, J=8.1 Hz), 6.70 (1H, s), 7.73 (1H, d, J=8.1 Hz), 9.29 (1H, s), 9.84 (1H, s)

EXAMPLE 8

To 100 ml of dioxane, there were added 13.8 g (112 mmol) of 6-amino-m-cresol and 5.85 g (58.5 mmol) of calcium carbonate, followed by cooling in an ice bath. To the obtained solution, there was added dropwise 16.0 g of acetoxyacetyl chloride over 10 minutes. Then the mixture was further stirred at room temperature for 10 minutes. After adding 100 ml of acetone thereto, the inorganic salt was filtered and washed with 50 ml of acetone. The filtrate was combined with the washing liquor and the solvent was distilled off therefrom under reduced pressure. Thus 20.6 g (92.4 mmol) of N-(2-hydroxy-4-methylphenyl)acetoxyacetamide was obtained as brown crystals. The yield was 82%. A 2.6 g portion of these crystals were recrystallized from acetonitrile. Thus 1.2 g of N-(2-hydroxy-4-methylphenyl)acetoxyacetamide was obtained as pale purple crystals. The recovering yield was 42%.

$^1$H-NMR spectrum (200 MHz, DMSO-d$_6$): δppm: 2.10 (3H, s), 2.19 (3H, s), 4.67 (2H, s), 6.56 (1H, d, J=8.0 Hz), 6.68 (1H, s), 7.63 (1H, d, J =8.0 Hz), 9.21 (1H, s), 9.74 (1H, s)

EXAMPLE 9

To 100 ml of methanol, there were added 18.0 g (80.7 mmol) of N-(2-hydroxy-4-methylphenyl)acetoxyacetamide and 12.0 g of potassium carbonate, followed by stirring at room temperature for 14 hours. Then 150 ml of water was added thereto and the mixture was neutralized with glacial acetic acid and extracted with 200 ml of ethyl acetate twice. After washing with a saturated aqueous solution of common salt and dried over anhydrous Glauber's salt, the solvent was distilled off under reduced pressure to give thereby brown crystals. These crystals were subjected to silica gel column chromatography (Si60 manufactured by Merck; 230–400 mesh; 200 g; eluent: ethyl acetate). From the 0 to 3,500 ml fraction, the solvent was distilled off under reduced pressure, followed by drying. Thus 7.79 g (53.3 mmol) of N-(2-hydroxy-4-methylphenyl)hydroxyacetamide was obtained as a brown solid. The yield was 53%. A 6.81 g portion of this product was recrystallized from acetonitrile to give thereby 4.73 g of N-(2-hydroxy-4-methylphenyl)hydroxyacetamide as pale brown crystals. The recovering yield was 69%.

$^1$H-NMR spectrum (200 MHz, DMSO-d$_6$): δppm: 2.17 (3H, s), 3.94 (2H, d, J=4.2 Hz), 6.05 (1H, brt, J=4.2 Hz), 6.57 (1H, d, J=8.1 Hz), 6.68 (1H, s), 7.99 (1H, d, J=8.1 Hz), 9.07 (1H, s), 9.96 (1H, s)

EXAMPLE 10

To 50 ml of dioxane, there were added 5.20 g (42.3 mmol) of 6-amino-m-cresol and 2.33 g (23.3 mmol) of calcium carbonate. To the obtained solution, there was added dropwise 5.00 g (46.5 mmol) of methoxyacetyl chloride over 10 minutes. After stirring at room temperature for 20 minutes, 50 ml of acetone was added thereto. The inorganic salt was filtered and washed with 20 ml of acetone. The filtrate was combined with the washing liquor and the solvent was distilled therefrom under reduced pressure. Thus 5.91 g (30.3 mmol) of N-(2-hydroxy-4-methylphenyl)methoxyacetamide was obtained as a brown solid. The yield was 72%. This product was recrystallized from acetonitrile to give thereby 2.66 g of N-(2-hydroxy-4-methylphenyl)methoxyacetamide as pale brown crystals. The recovering yield was 45%.

$^1$H-NMR spectrum (200 MHz, DMSO-d$_6$): δppm: 2.19 (3H, s), 3.42 (3H, s), 3.98 (2H, s), 6.59 (1H, d, J=8.2 Hz), 6.69 (1H, s), 7.90 (1H, d, J=8.2 Hz), 8.83 (1H, s) 9.96 (1H, s)

EXAMPLE 11

(i) To 50 ml of ethyl acetate, there were added 4.27 g (24.4 mmol) of N-(tert-butoxycarbonyl)glycine and 5.03 g (24.4 mmol) of N,N'-dicyclohexyl carbodiimide and stirred at room temperature for 30 minutes. The obtained solution was cooled in an ice bath and 3.00 g (24.4 mmol) of 6-amino-m-cresol and 2.51 g (24.4 mmol) of triethylamine were added thereto. After putting back to room temperature, the mixture was stirred for 12 hours. After the completion of the reaction, 50 ml of N,N-dimethylformamide was added thereto and the crystals thus precipitated were filtered and washed with 20 ml of N,N-dimethylformamide. The filtrate was combined with the washing liquor and the solvent was distilled off therefrom under reduced pressure to thereby give a brown solid. This product was subjected to silica gel column chromatography (Si60 manufactured by Merck; 230–400 mesh; 300 g; eluent: 3% methanol-chloroform). From the 900–1,300 ml fraction, the solvent was distilled off under reduced pressure and 20 ml of chloroform was added thereto to cause thereby crystallization. After filtering and drying, 2.00 g (7.1 mmol) of N-(2-hydroxy-4-methylphenyl)-tert-butoxycarbonylaminoacetamide was obtained as yellow crystals. The yield was 29%.

$^1$H-NMR spectrum (200 MHz, DMSO-d$_6$): δppm: 1.40 (9H, s), 2.18 (3H, s), 3.70 (2H, d, J=5.9 Hz), 6.57 (1H, d, J=8.0 Hz), 6.66 (1H, s), 7.29 (1H, t, J=5.9 Hz), 7.76 (1H, d, J=8.0 Hz), 8.94 (1H, s), 9.80 (1H, brs)

(ii) To 30 ml of a saturated solution of hydrogen chloride in ether, there was added 1.80 g (6.4 mmol) of N-(2-hydroxy-4-methylphenyl)-tert-butoxycarbonylaminoacetamide and stirred at room temperature for 20 minutes. After the completion of the reaction, the crystals thus precipitated were filtered, washed with ether and dried. Thus 1.21 g (5.6 mmol) of N-(2-hydroxy-4-methylphenyl)aminoacetamide hydrochloride was obtained as colorless crystals. The yield was 87%.

$^1$H-NMR spectrum (200 MHz, DMSO-d$_6$): δppm: 2.19 (3H, s), 3.80 (2H, br), 6.58 (1H, d, J=8.1 Hz), 6.75 (1H, s), 7.68 (1H, d, J=8.1 Hz), 8.25 (3H, br), 9.72 (1H, s), 9.92 (1H, s)

EXAMPLE 12

To a mixture of 15 ml of ethanol with 15 ml of water, there was added 20.0 g (163 mmol) of 6-amino-m-cresol. To the solution thus obtained, there was added dropwise 22.2 g (171 mmol) of propionic anhydride over 30 minutes. After stirring at room temperature for 20 minutes, 15 ml of water was added thereto. The crystal thus precipitated were filtered and recrystallized from a solvent mixture of ethanol and water (7:8 (v:v)). Thus 21.8 g (122 mmol) of N-(2-hydroxy-4-methylphenyl)propionamide was obtained as colorless crystals. The yield was 75%.

$^1$H-NMR spectrum (200 MHz, DMSO-d$_6$): δppm: 1.07 (3H, t, J=7.3 Hz), 2.19 (3H, s), 2.36 (2H, q, J=7.3 Hz), 6.57 (1H, d, J=8.0 Hz), 6.67 (1H, s), 7.49 (1H, d, J=8.0 Hz), 9.19 (1H, s), 9.61 (1H, s)

EXAMPLE 13

To 20 ml of ethanol, there were added 6.72 g of sodium methoxide, 20.0 g (169 mmol) of ethyl lactate and 6.95 g (56.5 mmol) of 6-amino-m-cresol, followed by heating under reflux for 3 hours. After cooling, 100 ml of water was added to the mixture and the crystals thus precipitated were filtered. The filtrate was extracted with 200 ml of ethyl acetate, washed with a saturated aqueous solution of common salt and dried over anhydrous Glauber's salt. After distilling off the solvent under reduced pressure, the solid thus obtained was subjected to silica gel column chromatography (Si60 manufactured by Merck; 230–400 mesh; 300 g; eluent: 2% methanol-chloroform). After distilling off the solvent from the 2,000–3,200 ml fraction under reduced pressure, the obtained solid was dissolved in 200 ml of ethyl acetate, washed with 1N hydrochloric acid, a saturated aqueous solution of sodium hydrogencarbonate and a saturated aqueous solution of common salt and dried over anhydrous Glauber's salt. After distilling off the solvent under reduced pressure, the residue was dried and thus 0.70 g (3.6 mmol) of N-(2-hydroxy-4-methylphenyl)-2-hydroxypropionamide was obtained as brown crystals. The yield was 6%.

$^1$H-NMR spectrum (200 MHz, DMSO-d$_6$): δppm: 1.31 (3H, d, J=6.8 Hz), 2.19 (3H, s), 4.12 (1H, qd, J=6.8, 6.8 Hz), 6.18 (1H, d, J=6.8 Hz), 6.58 (1H, d, J=8.1 Hz), 6.69 (1H, s), 8.02 (1H, d, J=8.1 Hz), 9.17 (1H, s), 9.97 (1H, s)

EXAMPLE 14

(i) To 50 ml of ethyl acetate, there were added 4.61 g (24.4 mmol) of N-(tert-butoxycarbonyl)-β-alanine and 5.03 g (24.4 mmol) of N,N'-dicyclohexyl carbodiimide and stirred at room temperature for 30 minutes. To the solution thus obtained, there were added 3.00 g (24.4 mmol) of 6-amino-m-cresol and 2.51 g (24.4 mmol) of triethylamine and stirred at room temperature for 17 hours. After the completion of the reaction, 100 ml of ethyl acetate was added to the solution. After filtering insoluble crystals, the filtrate was washed with 1N hydrochloric acid, a saturated aqueous solution of sodium hydrogencarbonate and a saturated aqueous solution of common salt and dried over anhydrous Glauber's salt. After distilling off the solvent under reduced pressure, the brown solid thus obtained was subjected to silica gel column chromatography (Si60 manufactured by Merck; 230–400 mesh; 300 g; eluent: 5% methanol-chloroform). After distilling off the solvent from the 600–1,200 ml fraction under reduced pressure, pale brown crystals were obtained. These crystals were recrystallized from chloroform and thus 1.56 g (5.3 mmol) of N-(2-hydroxy-4-methylphenyl)-3-(tert-butoxy-carbonyl)aminopropionamide was obtained as pale brown crystals. The yield was 22%.

$^1$H-NMR spectrum (200 MHz, DMSO-d$_6$): δppm: 1.37 (9H, s), 2.19 (3H, s), 2.50 (2H, t, J=7.0 Hz), 3.20 (2H, td, J=7.0, 6.0 Hz), 6.57 (1H, d, J=8.1 Hz), 6.67 (1H, s), 6.84 (1H, brt, J=6.0 Hz), 7.50 (1H, d, J=8.1 Hz), 9.24 (1H, s), 9.60 (1H, s)

(ii) To 15 ml of a saturated solution of hydrogen chloride in ether, there were added 10 ml of acetone and 1.30 g (4.4 mmol) of N-(2-hydroxy-4-methylphenyl)-3-(tert-butoxycarbonyl)aminopropionamide and stirred at room temperature for 30 minutes. After the completion of the reaction, the crystals thus precipitated were filtered, washed with ether and dried. Thus 0.76 g (2.6 mmol) of N-(2-hydroxy-4-methylphenyl)-3-aminopropionamide hydrochloride was obtained. The yield was 59%.

$^1$H-NMR spectrum (200 MHz, DMSO-d$_6$): δppm: 2.19 (3H, s), 2.78 (2H, t, J=6.7 Hz), 3.03 (2H, m), 6.56 (1H, d, J=8.1 Hz), 6.72 (1H, s), 7.56 (1H, d, J=8.1 Hz), 8.06 (3H, br), 9.52 (1H, s), 9.72 (1H, s)

EXAMPLE 15

To 30 ml of dioxane, there were added 1.50 g (12.6 mmol) of 6-amino-m-cresol and 0.6 g (6.0 mmol) of calcium carbonate. To the solution thus obtained, there was added 1.02 g of butanoyl chloride over 10 minutes, followed by stirring at room temperature for 30 minutes. After the completion of the reaction, the inorganic salt was filtered and 150 ml of water was poured thereto. Then the mixture was extracted with 150 ml of ethyl acetate, washed with a saturated aqueous solution of common salt and dried over anhydrous Glauber's salt. After distilling off the solvent under reduced pressure, a red oily product was obtained. This product was crystallized by adding thereto 15 ml of hexane and 6 ml of ethyl acetate, and then filtered and dried. Thus 0.62 g (3.2 mmol) of N-(2-hydroxy-4-methylphenyl)butanamide was obtained as colorless crystals. The yield was 25%.

$^1$H-NMR spectrum (200 MHz, DMSO-d$_6$): δppm: 0.91 (3H, t, J=7.3 Hz), 1.59 (2H, qt, J=7.3, 7.3 Hz), 2.19 (3H, s), 2.34 (2H, t, J=7.3 Hz), 6.57 (1H, d, J=8.1 Hz), 6.66 (1H, s), 7.47 (1H, d, J=8.1 Hz), 9.24 (1H, s), 9.64 (1H, s)

EXAMPLE 16

To 100 ml of dioxane, there were added 15.0 g (122 mmol) of 6-amino-m-cresol and 7.58 g (75.8 mmol) of calcium carbonate and heated to 80° C. To the obtained solution, there was added 18.3 g (130 mmol) of 4-chlorobutanoyl chloride over 10 minutes and further stirred at 80° C. for 2 hours. After cooling and filtering the inorganic salt, the filtrate was poured into 500 ml of water, extracted with 200 ml of ethyl acetate and dried over anhydrous Glauber's salt. After distilling off the solvent under reduced pressure, a brown oily product was obtained. Then this product was crystallized from acetonitrile, filtered and dried to give thereby 8.4 g (36.1 mmol) of N-(2-hydroxy-4-methylphenyl)-4-chlorobutanamide as pale red crystals. The yield was 30%.

$^1$H-NMR spectrum (200 MHz, DMSO-d$_6$): δppm: 2.02 (2H, tt, J=7.1, 6.1 Hz), 2.19 (3H, s), 2.53 (2H, t, J=7.1 Hz), 3.69 (2H, t, J=6.1 Hz), 6.57 (1H, d, J=8.0 Hz), 6.67 (1H, s), 7.50 (1H, d, J=8.0 Hz), 9.28 (1H, s), 9.60 (1H, br)

EXAMPLE 17

To 200 ml of chloroform, there were added 20.0 g (163 mmol) of 6-amino-m-cresol and 17.9 g (179 mmol) of succinic anhydride and heated under reflux for 1 hour. After cooling, the crystals thus precipitated were filtered and recrystallized from a solvent mixture of acetonitrile-methanol (8:1 (v:v)). Thus 21.8 g (97.6 mmol) of N-(2-hydroxy-4-methyl-phenyl)succinamide was obtained as pale yellow crystals. The yield was 60%.

¹H-NMR spectrum (200 MHz, DMSO-d$_6$): δppm: 2.17 (3H, s), 2.49 (2H, t, J=5.5 Hz), 2.61 (2H, t, J=5.5 Hz), 6.55 (1H, d, J=8.1 Hz), 6.65 (1H, s), 7.51 (1H, d, J=8.1 Hz), 9.26 (1H, s), 9.60 (1H, s), 12.12 (1H, br)

EXAMPLE 18

(i) To 50 ml of acetic anhydride, there were added 2.50 g (13.8 mmol) of 5-isopropyl-2-nitrophenol and 0.3 ml of conc. sulfuric acid and stirred at room temperature for 2.5 hours. Then the reaction mixture was poured into 150 ml of water and stirred at room temperature for 2 hours. Then it was extracted with 150 ml of ethyl acetate, washed with a saturated aqueous solution of sodium hydrogencarbonate and a saturated aqueous solution of common salt and dried over anhydrous Glauber's salt. After distilling off the solvent under reduced pressure and drying, 3.08 g (13.8 mmol) of 5'-isopropyl-2'-nitrophenyl acetate was obtained as a yellow oily product. The yield was 100%.

(ii) To 150 ml of ethanol, there were added 3.00 g (13.5 mmol) of 5'-isopropyl-2'-nitrophenyl acetate and 0.3 g of 5% palladium carbon and stirred under a hydrogen pressure of 50 kg/cm$^2$ at 60° C. for 4 hours. After cooling and filtering the catalyst, the solvent was distilled off from the filtrate under reduced pressure. Thus 2'-amino-5'-isopropylphenyl acetate was obtained as a brown solid.

To the obtained product, there were added 25 ml of acetic anhydride and 0.5 ml of conc. sulfuric acid and stirred at room temperature for 20 minutes. After the completion of the reaction, 280 ml of water was added thereto and the mixture was stirred at room temperature for 30 minutes. Then it was extracted with 200 ml of ethyl acetate, washed with a saturated aqueous solution of common salt and dried over anhydrous Glauber's salt. After distilling off the solvent under reduced pressure, 2'-acetamide-5'-isopropylphenyl acetate was obtained as a brown oily product.

This product was dissolved in 30 ml of methanol and 6.0 g of potassium hydroxide and 50 ml of water were added thereto, followed by stirring at room temperature for 20 minutes. After the completion of the reaction, the mixture was neutralized with glacial acetic acid, poured into 100 ml of water and extracted with 150 ml of ethyl acetate. Then it was washed with a saturated aqueous solution of common salt and dried over anhydrous Glauber's salt. After distilling off the solvent under reduced pressure, a brown oily product was obtained. This product was subjected to silica gel column chromatography (Si60 manufactured by Merck; 230–400 mesh; 300 g; eluent: hexane-ethyl acetate (2:3 (v:v)). The solvent was distilled off from the 600–1,200 ml fraction under reduced pressure and thus a pale brown oily product was obtained. This product was dissolved in 10 ml of ethyl acetate and crystallized by adding 20 ml of hexane. The crystals were filtered, washed with hexane and dried to give thereby 0.41 g (2.1 mmol) of N-(2-hydroxy-4-isopropylphenyl)acetamide as pale brown crystals. The yield from 5'-isopropyl-2'-nitrophenyl acetate was 16%.

¹H-NMR spectrum (200 MHz, DMSO-d$_6$): δppm: 1.14 (6H, d, J=6.8 Hz), 2.06 (3H, s), 2.75 (1H, sep, J=6.8 Hz), 6.62 (1H, d, J=8.2 Hz), 6.70 (1H, S), 7.47 (1H, d, J=8.2 HZ), 9.33 (1H, s), 9.61 (1H, S)

EXAMPLE 19

TO 5.0 ml of acetic anhydride, there were added 1.00 g (8.1 mmol) of 6-amino-m-cresol and 0.2 ml of conc. sulfuric acid and stirred at room temperature for 1 hour. Then 30 ml of water was added thereto and stirred for 10 hours. The crystals thus precipitated were filtered, washed with water and recrystallized from ethanol. Thus 0.75 g (3.6 mmol) of 2'-acetamide-5'-methylphenyl acetate was obtained as colorless needle-like crystals. The yield was 44%.

¹H-NMR spectrum (200 MHz, DMSO-d$_6$): δppm: 2.04 (3H, s), 2.26 (3H, s), 2.27 (3H, s), 6.93 (1H, s), 7.00 (1H, d, J=8.2 Hz), 7.71 (1H, d, J=8.2 Hz), 9.34 (1H, s)

EXAMPLE 20

To 5.0 ml of propionic anhydride, there were added 1.00 g (8.1 mmol) of 6-amino-m-cresol and 0.2 ml of conc. sulfuric acid and stirred at room temperature for 1 hour. After adding 30 ml of water, the mixture was further stirred for 8 hours. The crystals thus precipitated were filtered, washed with water and recrystallized from ethanol. Thus 0.82 g (3.1 mmol) of 2'-propionamide-5'-methylphenyl propionate was obtained as colorless needle-like crystals. The yield was 39%.

¹H-NMR spectrum (200 MHz, DMSO-d$_6$): δppm: 1.05 (3H, t, J=7.6 Hz), 1.12 (3H, t, J=7.5 Hz), 2.26 (3H, s), 2.30 (2H, q, J=7.6 Hz), 2.60 (2H, q, J=7.6 Hz), 6.95 (1H, s), 6.99 (1H, d, J=8.2 Hz), 7.63 (1H, d, J=8.2 Hz), 9.22 (1H, s)

EXAMPLE 21

(i) To 100 ml of methanol, there were added 24.6 g (95.0 mmol) of 4-benzyloxy-2-methyl-5-nitrophenol and 6.38 g (114 mmol) of potassium hydroxide and heated under reflux. To the obtained solution, there was added 14.4 g (114 mmol) of dimethyl sulfate and heated under reflux for additional one hour. After cooling and adding 200 ml of water, the crystals thus precipitated were filtered and recrystallized from hexane-acetone (2:1 (v:v)). Thus 13.0 g (47.5 mmol) of 4-benzyloxy-2-methyl-5-nitrosoanisole was obtained as yellow crystals. The yield was 50%.

¹H-NMR spectrum (200 MHz, DMSO-d$_6$): δppm: 2.22 (3H, s), 3.81 (3H, s), 5.23 (2H, s), 7.36 (1H, s), 7.40 (1H, s), 7.45 (4H, s)

(ii) To an autoclave, there were fed 1.2 g of 10% palladium carbon, 8.3 g (30.4 mmol) of 4-benzyloxy-2-methyl-5-nitrosoanisole and 250 ml of ethanol and stirred under a hydrogen pressure of 50 kg/cm$^2$ at 50° C. for 6 hours. After cooling and filtering the palladium carbon, 3.72 g (36.5 mmol) of acetic anhydride was added to the filtrate and stirred at room temperature for 20 minutes. After the completion of the reaction, the solvent was distilled off under reduced pressure and thus a brown solid was obtained. This product was recrystallized from acetonitrile to give thereby 3.87 g (19.8 mmol) of N-(2-hydroxy-5-methoxy-4-methylphenyl)acetamide as colorless crystals. The yield was 65%.

¹H-NMR spectrum (200 MHz, DMSO-d$_6$): δppm: 2.05 (3H, s), 2.08 (3H, s), 3.66 (3H, s), 6.64 (1H, s), 7.26 (1H, s), 9.12 (1H, s), 9.38 (1H, s)

EXAMPLE 22

(i) To 60 ml of acetone, there were added 25.0 g (175 mmol) of 4-chloro-3-methylphenol and 16.6 g (210 mmol) of pyridine. After ice-cooling, 21.9 g (193 mmol) of methanesulfonyl chloride was added thereto over 5 minutes. After further stirring at room temperature for 2 days, the reaction mixture was poured into 300 ml of water and extracted with 300 ml of ethyl acetate. After distilling off the solvent under reduced pressure, 38.7 g of 4'-chloro-3'-methylphenyl methanesulfonate was obtained as a colorless oily product.

(ii) To 130 ml of conc. sulfuric acid, there was added 38.7 g of the 4'-chloro-3'-methylphenyl methanesulfonate as obtained in the above (i) under ice-cooling. Further, 16 ml of conc. nitric acid was added thereto over 10 minutes under ice-cooling. After stirring for 20 minutes, the solution was poured into 600 ml of ice water and extracted with 300 ml of chloroform. The extract was washed with water and a saturated aqueous solution of sodium hydrogencarbonate and the solvent was distilled off under reduced pressure to thereby give a brown oily product. This product was then subjected to silica gel column chromatography (Si60 manufactured by Merck; 230-400 mesh; 200 g; eluent: hexane-ethyl acetate (4:1 (v:v)). The solvent was distilled off from the 500-2,500 ml fraction and thus 37.9 g of 4'-chloro-5'-methyl-2'-nitrophenyl methanesulfonate was obtained as a yellow oily product.

(iii) To 160 ml of methanol, there were added 37.9 g of the 4'-chloro-5'-methyl-2'-nitrophenyl methanesulfonate as obtained in the above (ii) and 80 ml of a 7N aqueous solution of sodium hydroxide, followed by heating under reflux for 20 minutes. After cooling, the reaction mixture was poured into 500 ml of water and neutralized with hydrochloric acid. The crystals thus precipitated were filtered and recrystallized from acetone to give thereby 10.4 g (55 mmol) of 4-chloro-5-methyl-2-nitrophenol as yellow crystals. The yield from 4-chloro-3-methylphenol was 31%.

$^1$H-NMR spectrum (200 MHz, DMSO-d$_6$): δppm: 2.31 (3H, s), 7.09 (1H, s), 7.92 (1H, s), 11.11 (1H, s)

(iv) To 15 ml of a solvent mixture of water-ethanol (1:1 (v:v)), there was added 0.5 ml of glacial acetic acid and heated under reflux. To the obtained solution, there were added 0.86 g of iron powder and 0.80 g (4.3 mmol) of 4-chloro-5-methyl-2-nitrophenol and the mixture was heated under reflux for additional 20 minutes. After cooling and adding 30 ml of acetone, the iron powder was filtered and washed with 50 ml of acetone. The filtrate was combined with the washing liquor and the solvent was distilled off therefrom under reduced pressure to thereby give a brown solid. The obtained product was subjected to silica gel column chromatography (Si60 manufactured by Merck; 230-400 mesh; 200 g; eluent: hexane-ethyl acetate (2:1 (v:v)). The solvent was distilled off from the 1,100-2,000 ml fraction and thus 0.29 g (1.8 mmol) of 2-amino-4-chloro-5-methylphenol was obtained as yellow crystals. The yield was 43%.

$^1$H-NMR spectrum (200 MHz, DMSO-d$_6$): δppm: 2.08 (3H, s), 4.57 (2H, brs), 6.55 (1H, s), 6.58 (1H, s), 9.13 (1H, br)

(v) To 30 ml of methanol, there were added 1.0 g (6.4 mmol) of 2-amino-4-chloro-5-methylphenol and 0.71 g (7.0 mmol) of acetic anhydride and stirred at room temperature for 30 minutes. To this solution, there was added 60 ml of water. The crystals thus precipitated were filtered and recrystallized from methanol. Thus 0.89 g (4.5 mmol) of N-(5-chloro-2-hydroxy-4-methylphenyl)acetamide was obtained as pale brown crystals. The yield was 70%.

$^1$H-NMR spectrum (200 MHz, DMSO-d$_6$): δppm: 2.07 (3H, s), 2.19 (3H, s), 6.79 (1H, s), 7.85 (1H, s), 9.25 (1H, s), 9.97 (1H, s)

EXAMPLE 23

Keratinous fiber dye composition:

A base of the following composition was prepared.

TABLE 1

| Component | Amount (% by weight) |
|---|---|
| Oleic acid | 10 |
| Oleic acid diethanolamide | 8 |
| Oleyl alcohol | 2 |
| Polyoxyethylene octyl dodecyl ether (average addition mole number of EO: 20) | 10 |
| Ethanol | 15 |
| Propylene glycol | 10 |
| Ammonium chloride | 3 |
| 25% Aqueous ammonia | 7 |
| water | 35 |
| Total | 100 |

To 100 g of the base of the above composition, there were added 0.005 mole of the developer and 0.005 mole of the coupler specified in Table 2 in the combination specified in Tables 3 and 4. Next, the composition was adjusted to pH 9.5 with ammonia. Thus a keratinous fiber dye composition according to the present invention was obtained.

To 100 g of the dye composition thus obtained, there was added the same weight of a 6% aqueous solution of hydrogen peroxide to give thereby a dyeing solution.

This dyeing solution was applied to grizzled human hair and allowed to stand at 30° C. for 30 minutes. After washing with a common shampoo and drying, the color tone, the color change/fading and the shampoo-resistance of the dyed hair thus obtained were evaluated by the test methods which will be specified below. Table 4 show the results.

TABLE 2

Developer:
    P$_1$: p-Phenylenediamine
    P$_2$: Toluene-2,5-diamine
Coupler:
    C$_1$: N-(2-Hydroxy-4-methylphenyl)formamide (Compound of the Invention)
    C$_2$: N-(2-Hydroxy-4-methyphenyl)methylcarbamate (Compound of the Invention)
    C$_3$: N-(2-Hydroxy-4-methylphenyl)urea (Compound of the Invention)
    C$_4$: N-(2-Hydroxy-4-methylphenyl)-N'-(2-hydroxyethyl)urea (Compound of the Invention)
    C$_5$: N-(2-Hydroxy-4-methylphenyl)acetamide (Compound of the Invention)
    C$_6$: N-(2-Hydroxy-4-methylphenyl)chloroacetamide (Compound of the Invention)
    C$_7$: N-(2-Hydroxy-4-methylphenyl)acetoxyacetamide (Compound of the Invention)
    C$_8$: N-(2-Hydroxy-4-methylphenyl)hydroxyacetamide (Compound of the Invention)
    C$_9$: N-(2-Hydroxy-4-methylphenyl)methoxyacetamide (Compound of the Invention)
    C$_{10}$: N-(2-Hydroxy-4-methylphenyl)aminoacetamide hydrochloride (Compound of the Invention)
    C$_{11}$: N-(2-Hydroxy-4-methylphenyl)propionamide (Compound of the Invention)
    C$_{12}$: N-(2-Hydroxy-4-methylphenyl)-2-hydroxypropionamide (Compound of the Invention)
    C$_{13}$: N-(2-Hydroxy-4-methylphenyl)-3-aminopropionamide hydrochloride (Compound of the Invention)
    C$_{14}$: N-(2-Hydroxy-4-methylphenyl)butanamide (Compound of the Invention)
    C$_{15}$: N-(2-Hydroxy-4-methylphenyl)-4-chlorobutanaide (Compound of the Invention)
    C$_{16}$: N-(2-Hydroxy-4-methylphenyl)succinamide (Compound of the Invention)
    C$_{17}$: N-(2-Hydroxy-4-isopropylphenyl)acetamide (Compound of the Invention)
    C$_{18}$: 2'-Acetamide-5'-methylphenyl acetate (Compound of the Invention)
    C$_{19}$: 2'-Propionamide-5'-methylphenyl propionate

TABLE 2-continued (Compound of the Invention)
C$_{20}$: N-(2-Hydroxy-5-methoxy-4-methylphenyl)acetamide
(Compound of the Invention)
C$_{21}$: N-(5-Chloro-2-hydroxy-4-methylphenyl)acetamide
(Compound of the Invention)
C$_{22}$: 2,6-Diaminopyridine (Comparative Compound)
C$_{23}$: m-Phenylenediamine (Comparative Compound)

Test method:

(1) Color change/fading resistance (fastness):

After storing at 40° C. under 75% RH for 60 hours and then drying at room temperature, a sample was compared with the naked eye to dyed tress which had been stored at −5° C., followed by evaluating based on the following criteria.
- A: Substantially no color change/fading
- B: Somewhat color change/fading
- C: Serious color change/fading (2) Shampoo resistance (fastness):

After repeatedly washing with a neutral shampoo 15 times, a sample was compared to untreated dyed tress with the naked eye, followed by evaluating based on the following criteria.
- A: Substantially no discoloration
- B: Somewhat discoloration
- C: Serious discoloration

TABLE 3

| Product of the Invention | Developer | Coupler | Color Tone |
|---|---|---|---|
| 1 | P$_1$ | C$_1$ | Blue |
| 2 | P$_1$ | C$_2$ | Blue |
| 3 | P$_1$ | C$_3$ | Blue |
| 4 | P$_1$ | C$_4$ | Blue |
| 5 | P$_1$ | C$_5$ | Blue |
| 6 | P$_1$ | C$_6$ | Blue |
| 7 | P$_1$ | C$_7$ | Blue |
| 8 | P$_1$ | C$_8$ | Blue |
| 9 | P$_1$ | C$_9$ | Blue |
| 10 | P$_1$ | C$_{10}$ | Yellowish Brown |
| 11 | P$_1$ | C$_{11}$ | Blue |
| 12 | P$_1$ | C$_{12}$ | Blue |
| 13 | P$_1$ | C$_{13}$ | Blue |
| 14 | P$_1$ | C$_{14}$ | Blue |
| 15 | P$_1$ | C$_{15}$ | Blue |
| 16 | P$_1$ | C$_{16}$ | Blue |
| 17 | P$_1$ | C$_{17}$ | Yellowish Green |
| 18 | P$_1$ | C$_{18}$ | Blue |
| 19 | P$_1$ | C$_{19}$ | Blue |
| 20 | P$_1$ | C$_{20}$ | Blue |
| 21 | P$_1$ | C$_{21}$ | Blue |
| 22 | P$_2$ | C$_1$ | Blue |
| 23 | P$_2$ | C$_2$ | Blue |
| 24 | P$_2$ | C$_3$ | Blue |
| 25 | P$_2$ | C$_4$ | Blue |
| 26 | P$_2$ | C$_5$ | Blue |
| 27 | P$_2$ | C$_6$ | Blue |
| 28 | P$_2$ | C$_7$ | Blue |
| 29 | P$_2$ | C$_8$ | Blue |
| 30 | P$_2$ | C$_9$ | Blue |
| 31 | P$_2$ | C$_{10}$ | Yellowish Brown |
| 32 | P$_2$ | C$_{11}$ | Blue |
| 33 | P$_2$ | C$_{12}$ | Blue |
| 34 | P$_2$ | C$_{13}$ | Blue |
| 35 | P$_2$ | C$_{14}$ | Blue |
| 36 | P$_2$ | C$_{15}$ | Blue |
| 37 | P$_2$ | C$_{16}$ | Blue |
| 38 | P$_2$ | C$_{17}$ | Dark Green |
| 39 | P$_2$ | C$_{18}$ | Blue |
| 40 | P$_2$ | C$_{19}$ | Blue |
| 41 | P$_2$ | C$_{20}$ | Blue |
| 42 | P$_2$ | C$_{21}$ | Blue |

TABLE 4

Keratinous Fiber Dye Composition

| | Product of the Invention | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 11 | 12 | 13 | 14 | 15 | 16 |
| Developer | P$_1$ | P$_1$ | P$_1$ | P$_1$ | P$_1$ | P$_1$ | P$_1$ | P$_1$ | P$_1$ | P$_1$ | P$_1$ | P$_1$ | P$_1$ | P$_1$ | P$_1$ |
| Coupler | C$_1$ | C$_2$ | C$_3$ | C$_4$ | C$_5$ | C$_6$ | C$_7$ | C$_8$ | C$_9$ | C$_{11}$ | C$_{12}$ | C$_{13}$ | C$_{14}$ | C$_{15}$ | C$_{16}$ |
| Color tone | Blue | Blue | Blue | Blue | Blue | Blue | Blue | Blue | Blue | Blue | Blue | Blue | Blue | Blue | Blue |
| Color change-/fading resistance | A | A | A | A | A | A | A | A | A | A | A | A | A | B | A |
| Shampoo resistance | B | A | A | A | A | A | A | A | A | A | A | A | A | A | A |

| | Product of the Invention | | | | | | | | | | | | | | |
|---|---|---|---|---|---|---|---|---|---|---|---|---|---|---|---|
| | 18 | 19 | 20 | 21 | 22 | 23 | 24 | 25 | 26 | 27 | 28 | 29 | 30 | 32 | 33 |
| Developer | P$_1$ | P$_1$ | P$_1$ | P$_1$ | P$_2$ | P$_2$ | P$_2$ | P$_2$ | P$_2$ | P$_2$ | P$_2$ | P$_2$ | P$_2$ | P$_2$ | P$_2$ |
| Coupler | C$_{18}$ | C$_{19}$ | C$_{20}$ | C$_{21}$ | C$_1$ | C$_2$ | C$_3$ | C$_4$ | C$_5$ | C$_6$ | C$_7$ | C$_8$ | C$_9$ | C$_{11}$ | C$_{12}$ |
| Color tone | Blue | Blue | Blue | Blue | Blue | Blue | Blue | Blue | Blue | Blue | Blue | Blue | Blue | Blue | Blue |
| Color change-/fading resistance | A | A | A | A | A | A | A | A | A | A | A | A | A | A | A |
| Shampoo resistance | A | A | A | A | B | A | A | A | A | A | A | A | A | A | A |

| | Product of the Invention | | | | | | | | Comparative Product | | | |
|---|---|---|---|---|---|---|---|---|---|---|---|---|
| | 34 | 35 | 36 | 37 | 39 | 40 | 41 | 42 | 1 | 2 | 3 | 4 |
| Developer | P$_2$ | P$_2$ | P$_2$ | P$_2$ | P$_2$ | P$_2$ | P$_2$ | P$_2$ | P$_2$ | P$_2$ | P$_1$ | P$_1$ |
| Coupler | C$_{13}$ | C$_{14}$ | C$_{15}$ | C$_{16}$ | C$_{18}$ | C$_{19}$ | C$_{20}$ | C$_{21}$ | C$_{22}$ | C$_{23}$ | C$_{22}$ | C$_{23}$ |
| Color tone | Blue | Blue | Blue | Blue | Blue | Blue | Blue | Blue | Blue | Blue | Blue | Blue |
| Color change-/fading resistance | A | A | B | A | A | A | A | A | B | C | B | C |
| Shampoo resistance | A | A | A | A | A | A | A | A | C | C | C | C |

Based on these results, it has been proved that the products according to the present invention are excellent in fastness. Further, the products according to the present invention impart a color tone of a high chroma to keratinous fibers and show a good coloring power.

While the invention has been described in detail and with reference to specific embodiments thereof, it will be apparent to one skilled in the art that various changes and modifications can be made therein without departing from the spirit and scope thereof.

What is claimed is:

1. A keratinous fiber dye composition comprising an aromatic diamine developer and a coupler, wherein said coupler is a 2-substituted amino-5-alkylphenol derivative represented by the following formula (1):

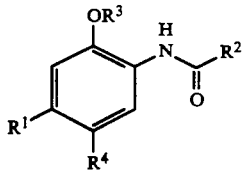

(1)

wherein $R^1$ represents an alkyl group having from 1 to 4 carbon atoms; $R^2$ represents a hydrogen atom, a substituted or unsubstituted alkyl group having from 1 to 4 carbon atoms, a substituted or unsubstituted alkoxy group having from 1 to 4 carbon atoms or a substituted or unsubstituted amino group; $R^3$ represents a hydrogen atom or a substituted or unsubstituted acyl group having from 2 to 5 carbon atoms; and $R^4$ represents a hydrogen atom, a halogen atom or an alkoxy group having from 1 to 4 carbon atoms which may be substituted with a hydroxyl group; or a cosmetically acceptable salt thereof, wherein the molar ratio of said developer to said coupler is from about 1:0.5 to 1:2.

2. The keratinous fiber dye composition of claim 1, wherein said developer is a compound represented by the following formula (2):

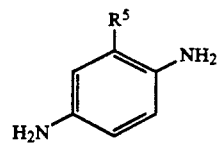

(2)

wherein $R^5$ is selected from the group consisting of a hydrogen atom, a methyl group, a methoxy group and a chlorine atom.

3. A method for dyeing a keratinous fiber which comprises applying to the keratinous fiber a composition comprising an aromatic diamine developer and a coupler, wherein said coupler is a 2-substituted amino-5-alkylphenol derivative represented by the following formula (1):

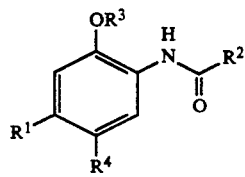

(1)

wherein $R^1$ represents an alkyl group having from 1 to 4 carbon atoms; $R^2$ represents a hydrogen atom, a substituted or unsubstituted alkyl group having from 1 to 4 carbon atoms, a substituted or unsubstituted alkoxy group having from 1 to 4 carbon atoms or a substituted or unsubstituted amino group; $R^3$ represents a hydrogen atom or a substituted or unsubstituted acyl group having from 2 to 5 carbon atoms; and $R^4$ represents a hydrogen atom, a halogen atom or an alkoxy group having from 1 to 4 carbon atoms which may be substituted with a hydroxyl group; or a cosmetically acceptable salt thereof, wherein the molar ratio of said developer to said coupler is from about 1:0.5 to 1:2.

4. The method of claim 3, wherein said developer is a compound represented by the following formula (2):

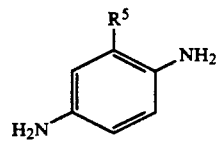

(2)

wherein $R^5$ is selected from the group consisting of a hydrogen atom, a methyl group, a methoxy group and a chlorine atom.

* * * * *